(12) United States Patent
Nagel et al.

(10) Patent No.: US 8,679,395 B2
(45) Date of Patent: Mar. 25, 2014

(54) MEDICAMENT CONTAINER

(75) Inventors: Thomas Nagel, Tharandt (DE); René Richter, Tharandt (DE); Robert Witt, Dresden (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 13/384,038

(22) PCT Filed: Jul. 14, 2010

(86) PCT No.: PCT/EP2010/060124
§ 371 (c)(1),
(2), (4) Date: Mar. 30, 2012

(87) PCT Pub. No.: WO2011/006922
PCT Pub. Date: Jan. 20, 2011

(65) Prior Publication Data
US 2012/0179094 A1 Jul. 12, 2012

(30) Foreign Application Priority Data

Jul. 14, 2009 (EP) .................................... 09009187

(51) Int. Cl.
*H05B 7/00* (2006.01)
(52) U.S. Cl.
USPC ............ 264/453; 264/478; 604/131; 604/132
(58) Field of Classification Search
USPC ............. 264/37.27, 37.33, 297.2, 328.1, 453, 264/478, 645; 604/68, 71, 75, 131, 132, 604/151, 186, 187, 256, 403
See application file for complete search history.

(56) References Cited

U.S. PATENT DOCUMENTS

| | | | | | |
|---|---|---|---|---|---|
| 1,731,703 | A | * | 10/1929 | Bourke | 222/99 |
| 2,805,662 | A | * | 9/1957 | Lawshe et al. | 604/204 |
| 3,838,794 | A | * | 10/1974 | Cogley et al. | 222/95 |
| 4,548,601 | A | * | 10/1985 | Lary | 604/204 |
| 4,784,857 | A | * | 11/1988 | Berry et al. | 424/449 |
| 4,898,582 | A | * | 2/1990 | Faste | 604/141 |
| 4,998,990 | A | * | 3/1991 | Richter et al. | 222/92 |
| 5,176,641 | A | * | 1/1993 | Idriss | 604/133 |
| 5,239,991 | A | * | 8/1993 | Chawla et al. | 128/203.15 |

(Continued)

FOREIGN PATENT DOCUMENTS

| | | |
|---|---|---|
| DE | 3541189 | 5/1987 |
| FR | 2633519 | 1/1990 |

(Continued)

OTHER PUBLICATIONS

International Search Report for International App. No. PCT/EP2010/060124, completed Oct. 22, 2010.

(Continued)

*Primary Examiner* — Nicholas Lucchesi
*Assistant Examiner* — Gerald Landry, II
(74) *Attorney, Agent, or Firm* — McDonnell Boehnen Hulbert & Berghoff LLP

(57) ABSTRACT

The invention relates to a medicament container, comprising a cavity at least partially defined by a container wall comprising a soft, flexible inner layer consisting of a soft material and a rigid outer layer consisting of a rigid material, wherein the layers are arranged as a one-piece part by two component injection molding.

11 Claims, 1 Drawing Sheet

(56) References Cited

U.S. PATENT DOCUMENTS

| | | | |
|---|---|---|---|
| 5,656,033 A * | 8/1997 | Atkinson | 604/141 |
| 5,906,592 A * | 5/1999 | Kriesel et al. | 604/132 |
| 6,264,977 B1 * | 7/2001 | Hoffmann | 424/447 |
| 7,357,276 B2 * | 4/2008 | Savage et al. | 222/92 |
| 2001/0016710 A1 * | 8/2001 | Nason et al. | 604/153 |
| 2003/0073952 A1 * | 4/2003 | Flaherty et al. | 604/151 |
| 2005/0006273 A1 * | 1/2005 | Chawla | 206/533 |
| 2005/0242114 A1 * | 11/2005 | Savage et al. | 222/92 |
| 2006/0172009 A1 * | 8/2006 | Chawla | 424/489 |
| 2006/0249419 A1 * | 11/2006 | Taylor et al. | 206/528 |
| 2007/0073263 A1 * | 3/2007 | Liu et al. | 604/408 |
| 2007/0112328 A1 * | 5/2007 | Steinbach et al. | 604/500 |
| 2008/0197045 A1 * | 8/2008 | Metzger et al. | 206/539 |
| 2009/0196675 A1 * | 8/2009 | May et al. | 401/206 |
| 2009/0317328 A1 * | 12/2009 | Arstad et al. | 424/1.89 |
| 2010/0004639 A1 * | 1/2010 | Pang et al. | 604/891.1 |
| 2010/0286639 A1 * | 11/2010 | Scholz et al. | 604/319 |
| 2011/0151259 A1 * | 6/2011 | Jarman-Smith et al. | 428/402 |

FOREIGN PATENT DOCUMENTS

| | | |
|---|---|---|
| GB | 990473 | 4/1965 |
| WO | 03/024511 | 3/2003 |
| WO | 2009/069518 | 6/2009 |

OTHER PUBLICATIONS

International Preliminary Report on Patentability for Int. App. No. PCT/EP2010/060124, mailed Jan. 26, 2012.

* cited by examiner

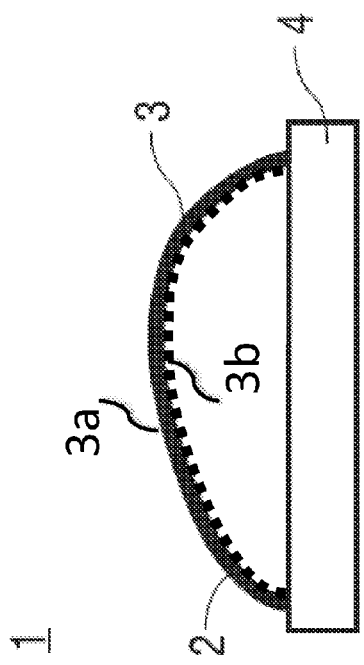
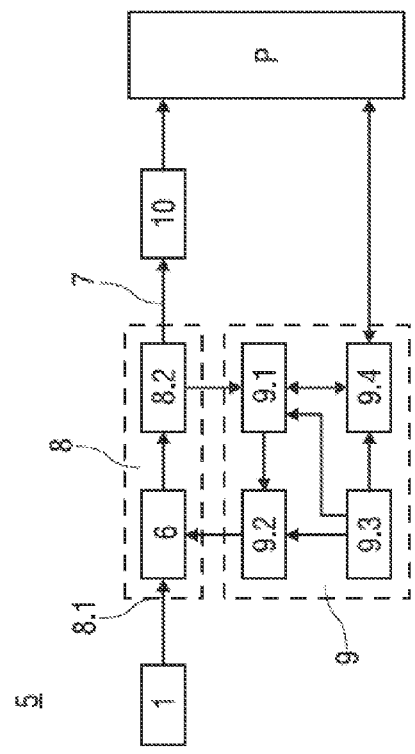

MEDICAMENT CONTAINER

CROSS REFERENCE TO RELATED APPLICATIONS

The present application is a U.S. National Phase Application pursuant to 35 U.S.C. §371 of International Application No. PCT/EP2010/060124 filed Jul. 14, 2010, which claims priority to European Patent Application No. 09009187.7 filed on Jul. 14, 2009. The entire disclosure contents of these applications are herewith incorporated by reference into the present application.

FIELD OF INVENTION

The invention relates to a medicament container for storing a liquid medicament comprising a cavity at least partially defined by a container wall.

BACKGROUND

Many medicaments have to be injected into the body. This applies in particular to medicaments, which are deactivated or have their efficiency remarkably decreased by oral administration, e.g. proteins (such as insulin, growth hormones, interferons), carbohydrates (e.g. heparin), antibodies and the majority of vaccines. Such medicaments are predominantly injected by means of syringes, medicament pens or medicament pumps.

Some medicaments have to be administered by inhaling them from so called inhalers.

WO 2009/069518 A1 discloses an inhaler, wherein the medicament to be inhaled is stored in a bag shaped medicament container.

U.S. Pat. No. 2,805,662 A discloses an ampoule having a tubular body, the upper part of which is relatively thin while a mating lower part is relatively thick. The upper part and the lower part are arranged as a one-piece part.

DE 35 41 189 A1 discloses an arrangement for injecting liquids, the arrangement having a medicament container comprising a cavity defined by a flexible container wall. The flexible container wall is assembled with a rigid mounting plate.

WO 03/024511 A1 discloses a medical fluid delivery device having a collapsible crushable enclosure wall formed of a laminate including an inner film layer of low density polyethylene bonded to an outer layer of cyclic olefin or cyclic olefin copolymer having a melting temperature of 1 to 10° C. greater than the melting temperature of the inner film layer. The outer film layer may be a blend of cyclic olefins or cyclic olefin copolymers and the inner film layer may comprise a first inner layer of linear low density polyethylene and an intermediate layer of high pressure low density polyethylene.

FR 2 633 519 discloses a syringe with a variable volume container for containing a liquid to be injected. The container wall is arranged in a bellows manner with flexible parts between two rigid plates.

U.S. Pat. No. 4,548,601 discloses a prepackaged, injectable pharmaceutical hypodermic needle having a semi-rigid outer container within which a substantially non-resiliant inner container is supported. The inner layer can collapse within the outer case which keeps its shape.

GB 990.473 discloses a medicament container comprising a cavity at least partially defined by a container wall comprising a soft, flexible wall portion and a rigid wall portion. The wall portions are arranged as a one-piece part by injection moulding.

SUMMARY

It is an object of the present invention to provide an improved medicament container.

The object is achieved by a medicament container according to claim 1.

Preferred embodiments of the invention are given in the dependent claims.

A medicament container according to the invention comprises a cavity at least partially defined by a container wall comprising a soft, flexible inner layer consisting of a soft material and a rigid outer layer consisting of a rigid material. The layers are arranged as a one-piece part by two component injection moulding. Two component injection moulding is a cost-saving method for producing the container. The outer layer serves for protecting the inner layer against ambient influences such as unintentional piercing.

An alternative method for producing the medicament container is coextrusion, wherein at least two different molten masses, e.g. plastic masses, are joined before leaving a moulding injection nozzle.

The medicament container may be filled with the respective medicament during production, i.e. two component injection moulding or coextrusion, of the container.

The cavity may be defined between the container wall and a rigid support consisting of the rigid material. The layers and the support may be arranged as a one-piece part by two component injection moulding or as mentioned above, by coextrusion. The support avoids sagging of the container due to gravity and improves a defined positioning of the container.

Preferably an interface for connecting a hollow needle or a pump to the cavity is arranged at the medicament container.

The interface may have the shape of an opening arranged in the container wall, wherein the opening is sealed by a septum, which may be pierced by a hollow needle. The septum may be crimped to the opening or attached in a different way.

In a preferred embodiment of the invention the rigid material is polypropylene or polyethylene.

An interior and/or an exterior of the container wall may be coated with silicone, particularly with food-grade silicone. Thus unintentional interaction between the medicament and the materials of the container wall and/or the support may be avoided, in particular when the medicament contains organic solvents.

The medicament container may be part of an injection arrangement for delivering a liquid medicament to a patient. The injection arrangement may further comprise a compression means for pressing the container wall against the rigid support, thereby displacing the fluid medicament from the medicament container.

The compression means may be a roller or wiper or shoe or an actuator which may be advanced so as to gradually reduce a volume of the medicament container, similar to the way a tube of tooth paste is squeezed.

Another injection arrangement may comprise the medicament container and a pump for pumping the liquid medicament from the medicament container to a medicament outlet. For example, the pump may be a micropump or a peristaltic pump.

The injection arrangement may be equipped with a hollow needle or an array of needles for piercing a patient's skin and administering the medicament or with a jet nozzle for forming a jet injector.

The medicament container may also be part of an inhaler arrangement.

The medicament container and/or the injection arrangement may be particularly used for storing or delivering one of an analgetic, an anticoagulant, insulin, an insulin derivate, heparin, Lovenox, a vaccine, a growth hormone, a peptide hormone, a proteine, and complex carbohydrates.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The present invention will become more fully understood from the detailed description given herein below and the accompanying drawings which are given by way of illustration only, and thus, are not limitative of the present invention, and wherein:

BRIEF DESCRIPTION OF THE FIGURES

FIG. 1 is a medicament container comprising a cavity defined by a container wall and a rigid support, FIG. 2 is a schematic view of an injection arrangement.

Corresponding parts are marked with the same reference symbols in all figures.

DETAILED DESCRIPTION

FIG. 1 shows a medicament container 1 comprising a cavity 2 defined by a container wall 3 and a rigid support 4.

The container wall 3 comprises a soft, flexible inner layer 3a consisting of a soft material and a rigid outer layer 3b consisting of a rigid material.

The rigid support 4 also consists of the rigid material. The layers and the support are arranged as a one-piece part 3 by two component injection moulding.

The medicament container 1 may have an interface for connecting a hollow needle or a pump.

The interface may have the shape of an opening arranged in the container wall 3, wherein the opening is sealed by a septum, which may be pierced by a hollow needle. The septum may be crimped to the opening or attached in a different way.

The rigid material may be polypropylene or polyethylene.

An interior and/or an exterior of the container wall 3 may be coated with silicone, particularly with food-grade silicone.

The medicament container 1 may be part of an injection arrangement for delivering a liquid medicament to a patient. The injection arrangement may further comprise a compression means (not shown) for pressing the container wall 3 against the rigid support 4, thereby displacing the fluid medicament from the medicament container 1.

The compression means may be a roller or wiper or shoe or an actuator which may be advanced so as to gradually reduce a volume of the medicament container 1.

Another injection arrangement 5 is shown in FIG. 2. The injection arrangement 5 comprises the medicament container 1 and a pump 6 for pumping the liquid medicament from the medicament container 1 to a medicament outlet 7. For example, the pump 6 may be a micropump or a peristaltic pump.

The injection arrangement 5 may essentially comprise two sub-units, a pump unit 8 and a reusable backend 9.

The pump unit 8 is replaceably attachable to the reusable backend 9. The pump unit 8 comprises a medicament inlet 8.1, the medicament outlet 7 and the pump 6 for delivering the liquid medicament from the inlet 8.1 to the outlet 7.

The medicament container 1 may be comprised in the reusable backend 9 or in the pump unit 8. The reusable backend 9 further comprises a control unit 9.1, a drive unit 9.2 for driving the pump 6 and an energy source 9.3 for powering the drive unit 9.2.

The pump unit 8 further comprises a flow sensor 8.2 for determining a volume flow of the medicament. The flow sensor 8.2 is connectable to the control unit 9.1 thus allowing to control the volume of medicament to be delivered.

The pump unit 8 has easily disconnectable interfaces to the medicament container 1, the drive unit 9.2 and the control unit 9.1 on the one hand and to the hollow injection needle 10 on the other hand, e.g. by Luer-Lok® or Luer-Slip®.

The energy source 9.3 may be a galvanic cell or battery of galvanic cells in case the drive unit 9.2 comprises an electrical motor. Preferably, the energy source 9.3 is a rechargeable accumulator. The rechargeable accumulator may be replaceable or chargeable in place by an external charging device (not shown).

The reusable backend 9 may further have a user interface 9.4 for user interaction. This may comprise a dosing and/or trigger knob or wheel and/or a display, e.g for displaying a dose volume (not shown).

The reusable backend 9 may further comprise a viewing window (not shown) for inspecting the contents of the medicament container 1.

The medicament container 1 or the injection arrangement 5 may preferably be used for delivering one of an analgetic, an anticoagulant, insulin, an insulin derivate, heparin, Lovenox, a vaccine, a growth hormone and a peptide hormone.

For performing an injection a user sets a required target dose at the user interface 9.4. The required target dose is forwarded to the control unit 9.1 and stored there. As soon as the user triggers the injection arrangement 5, e.g by pressing the knob, the target dose is converted into a flow sensor setpoint and the drive unit 9.2 is started. The drive unit 9.2 converts the electrical energy provided by the energy source 9.3 into mechanical energy and forwards it to the pump 6. There the energy is again converted into fluidic energy causing a volume flow of the medicament. The integrated flow sensor 8.2 acquires the volume flow and forwards measurement values to the control unit 9.1. The measurement values, particularly when in the shape of increments corresponding to volume increments may be integrated by the control unit 9.1 and the drive unit 9.2 switched off upon delivery of the setpoint volume. After delivery the control unit 9.1 may generate a message for the user to be displayed by the display unit.

The injection arrangement 5 may be equipped with a hollow needle 10 or an array of needles for piercing a patient's P skin and administering the medicament or with a jet nozzle for forming a jet injector.

The medicament container 1 may also be part of an inhaler arrangement.

An alternative method for producing the medicament container 1 is coextrusion, wherein at least two different molten masses, e.g. plastic masses, are joined before leaving a moulding injection nozzle.

The medicament container 1 may be filled with the respective medicament during production, i.e. two component injection moulding or coextrusion, of the container.

The medicament container 1 and/or the injection arrangement 5 may be particularly used for storing or delivering one of an analgetic, an anticoagulant, insulin, an insulin derivate, heparin, Lovenox, a vaccine, a growth hormone, a peptide hormone, a proteine, and complex carbohydrates.

The term "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyhepta-decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(02)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(02)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The invention claimed is:

1. A medicament container, comprising
    a) a cavity having a volume at least partially defined by a container wall comprising an inner layer and an outer layer, wherein the layers are arranged as a one-piece part, characterized in that the inner layer is a soft, flexible layer consisting of a soft material and that the outer layer consists of a material more rigid than the inner layer and that will not change shape but can change position when subjected to an external squeezing or compression force, wherein the layers are integral and arranged as a laminate by two component injection moulding and are configured such that the container wall will collapse in a manner analogous to a tube of toothpaste being squeezed in order to reduce the volume of the cavity during medicament delivery; and
    b) a rigid support connected to the container wall to further define the cavity.

2. A medicament container according to claim 1, characterized in that an interface for connecting a hollow needle or a pump to the cavity is arranged.

3. A medicament container according to claim 1, characterized in that an opening is arranged in the container wall, wherein the opening is sealed by a septum.

4. A medicament container according to claim 3, characterized in that the septum is crimped to the opening.

5. A medicament container according to claim 1, characterized in that the outer layer is polypropylene or polyethylene.

6. A medicament container according to claim 1, characterized in that an interior and/or an exterior of the container wall are/is coated with silicone.

7. An injection arrangement for delivering a liquid medicament from a medicament container, comprising
    a) a cavity having a volume at least partially defined by a container wall comprising an inner layer and an outer layer, wherein the layers are arranged as a one-piece part, characterized in that the inner layer is a soft, flexible layer consisting of a soft material and that the outer layer consists of a material more rigid than the inner layer and that will not change shape but can change position when subjected to an external squeezing or compression force, wherein the layers are integral and arranged by two component injection moulding and are configured such that the container wall will collapse in a manner analogous to a tube of toothpaste being squeezed in order to reduce the volume of the cavity during medicament delivery;
    b) a rigid support connected to the container wall to further define the cavity; and
    c) an actuator configured to press the container wall against the rigid support, thereby displacing the fluid medicament from the medicament container.

8. An injection arrangement for delivering a liquid medicament to a patient, comprising
    a) a cavity having a volume at least partially defined by a container wall comprising an inner layer and an outer layer, wherein the layers are arranged as a one-piece part, characterized in that the inner layer is a soft, flexible layer consisting of a soft material and that the outer layer consists of a material more rigid than the inner layer and that will not change shape but can change position when subjected to an external squeezing or compression force, wherein the layers are integral and arranged by two component injection moulding and are configured such that the container wall will collapse in a manner analogous to a tube of toothpaste being squeezed in order to reduce the volume of the cavity during medicament delivery;
    b) a rigid support connected to the container wall to further define the cavity; and
    c) a pump for pumping the liquid medicament from the medicament container to a medicament outlet.

9. An injection arrangement according to claim 7, characterized in that a hollow needle for piercing a patient's skin and administering the medicament is provided.

10. An injection arrangement according to claim 7, characterized in that a jet nozzle is provided for administering the medicament.

11. An injection arrangement according to claim 7, characterized in that the actuator is a roller or wiper or shoe, which may be advanced so as to gradually reduce a volume of the medicament container.

* * * * *